(12) United States Patent
Ma et al.

(10) Patent No.: US 10,126,439 B2
(45) Date of Patent: Nov. 13, 2018

(54) RECONSTRUCTION WITH MULTIPLE PHOTOPEAKS IN QUANTITATIVE SINGLE PHOTON EMISSION COMPUTED TOMOGRAPHY

(71) Applicant: Siemens Medical Solutions USA, Inc., Malvern, PA (US)

(72) Inventors: Jun Ma, Palatine, IL (US); Alexander Hans Vija, Evanston, IL (US); Amos Yahil, Stony Brook, NY (US); Xing Rong, Schaumburg, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 19 days.

(21) Appl. No.: 15/316,107

(22) PCT Filed: Jun. 18, 2015

(86) PCT No.: PCT/IB2015/054590
§ 371 (c)(1),
(2) Date: Dec. 2, 2016

(87) PCT Pub. No.: WO2015/198189
PCT Pub. Date: Dec. 30, 2015

(65) Prior Publication Data
US 2017/0108596 A1 Apr. 20, 2017

Related U.S. Application Data

(60) Provisional application No. 62/015,572, filed on Jun. 23, 2014.

(51) Int. Cl.
*G01T 1/164* (2006.01)
*G01T 1/29* (2006.01)
(Continued)

(52) U.S. Cl.
CPC ............ *G01T 1/2985* (2013.01); *A61B 6/037* (2013.01); *A61B 6/482* (2013.01); *A61B 6/5205* (2013.01);
(Continued)

(58) Field of Classification Search
CPC ............ G06T 11/006; G06T 2211/408; G06T 2211/424
See application file for complete search history.

(56) References Cited

U.S. PATENT DOCUMENTS

| 8,897,528 B2 * | 11/2014 | Benson | G01N 23/046 382/131 |
| 2006/0098857 A1 * | 5/2006 | Hawman | G06T 11/006 382/131 |

(Continued)

FOREIGN PATENT DOCUMENTS

| HU | 227601 | 8/2011 |
| HU | 229592 | 1/2014 |
| WO | 2009030966 | 3/2009 |

OTHER PUBLICATIONS

Bruyant, P, "Analytic and iterative reconstruction algorithms in SPECT", The Journal of Nuclear Medicine, Society of Nuclear-Medicine, US, vol. 43, No. 10, Jan. 1, 2002, pp. 1343-1358.
(Continued)

*Primary Examiner* — Kiho Kim

(57) ABSTRACT

In quantitative SPECT with multiple photopeaks, the combination for the multiple photopeaks is performed within or as part of reconstruction rather than post-reconstruction. Reconstruction is performed iteratively, so the combination for the multiple photopeaks is performed within the iteration loop of the reconstruction, such as combining back projected feedback of the different photopeaks for updating the volume.

21 Claims, 1 Drawing Sheet

(51) Int. Cl.
  *A61B 6/03* (2006.01)
  *G06T 11/00* (2006.01)
  *A61B 6/00* (2006.01)
(52) U.S. Cl.
  CPC .......... *G06T 11/006* (2013.01); *A61B 6/4241* (2013.01); *G06T 2211/408* (2013.01); *G06T 2211/424* (2013.01)

(56) References Cited

U.S. PATENT DOCUMENTS

2007/0183642 A1    8/2007  Ye et al.
2011/0044546 A1*  2/2011  Pan ...................... G06T 11/006
    382/195
2014/0369581 A1*  12/2014  Fu ........................ G06T 11/006
    382/131

OTHER PUBLICATIONS

Karine Assie, et al: "A Preliminary Study of Quantitative Protocols in Indium 111 SPECT Using Computational Simulations and Phantoms", IEEE Transactions on Nuclear Science, IEEE Service Center, New York, NY, US, vol. 57, No. 3, Jun. 1, 2010, pp. 1096-1104.
International PCT Search Report and Written Opinion dated Sep. 24, 2015 (13 pages).
Search Report for Corresponding Hungarian Patent Application No. P1700023, dated Mar. 30, 2017.

* cited by examiner

RECONSTRUCTION WITH MULTIPLE PHOTOPEAKS IN QUANTITATIVE SINGLE PHOTON EMISSION COMPUTED TOMOGRAPHY

RELATED APPLICATIONS

The present patent document claims the benefit of the filing date under 35 U.S.C. § 119(e) of Provisional U.S. Patent Application Ser. No. 62/015,572, filed Jun. 23, 2014, which is hereby incorporated by reference.

BACKGROUND

The present embodiments relate to single photon emission computed tomography (SPECT). SPECT imaging uses a radioisotope or radiotracer to determine physiological function within a patient. A spatial distribution of the radioisotope is imaged for qualitative SPECT based on counts of emissions. For quantitative SPECT, the activity concentration or specific the uptake of the radiotracer by tissues in the body is measured. The activity concentration (i.e., the concentration of the radiotracer from different locations) is reconstructed from detected emissions. Given various modeling and unknowns in SPECT, general use of quantitative SPECT has been limited. For example, quantitative SPECT is only realized in industry for Tc-99m, which has a single emission photopeak (i.e., energy peak).

A wide range of isotopes (e.g., Lu-177, In-111, Sm-153) used in nuclear medicine emit photons with multiple photopeaks. Using a multiple photopeak radioisotope in qualitative SPECT, each photopeak is reconstructed separately, providing a separate reconstructed volume for each photopeak. The reconstructed voxels are then summed to improve signal-to-noise ratio. However, summing the output results of the reconstruction may not be useful in quantitative SPECT. Summing the output activity concentration from different photopeaks does not provide an accurate activity concentration for quantification.

BRIEF SUMMARY

By way of introduction, the preferred embodiments described below include methods, systems, and non-transitory computer readable media for quantitative SPECT with multiple photopeaks. The combination for the multiple photopeaks is performed within or as part of reconstruction rather than post-reconstruction. Reconstruction is performed iteratively, so the combination for the multiple photopeaks is performed within the iteration loop of the reconstruction, such as combining back projected feedback of the different photopeaks for updating the volume.

In a first aspect, a method is provided for quantitative SPECT with multiple photopeaks. A SPECT detector detects emissions from a patient. The emissions are at different photopeak ranges of an isotope with respective multiple photopeaks. In reconstruction, forward projecting for first and second of the different photopeak ranges is performed. Backward projecting combines feedback from the first and second photopeak ranges. An image is generated as a function of the reconstruction.

In a second aspect, a non-transitory computer readable storage medium has stored therein data representing instructions executable by a programmed processor for SPECT with multiple emission energies. The storage medium includes instructions for projecting separately for each of the multiple emission energies with operators for that energy, and combining gradients from results of the projecting for the multiple emission energies.

In a third aspect, a SPECT system is provided. A detector is for detecting emissions at first and second photopeaks from an isotope emitting at the first and second photopeaks. A processor is configured to reconstruct a distribution of the emissions in three dimensions from the emissions. The reconstruction uses a conjugate gradient, where the conjugate gradient is a function of the emissions at both the first and second photopeaks. A display configured to display an image from the reconstruction.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Reconstruction is performed with multiple photopeaks. By combining feedback from the different photopeaks within the reconstruction, one image is reconstructed for quantitative SPECT. The resulting image may have a more accurate activity concentration or specific uptake value as compared to using a radioisotope with a single photopeak. Reconstruction using photon counts from multiple photopeaks in a combined way may increase the signal-to-noise ratio and improve image quality and quantitative accuracy for SPECT imaging.

For each photopeak, the image volume is projected and back projected with photopeak specific system matrix or projection operators (e.g., projection operators modeling attenuation correction, scatter correction, point response function, and/or sensitivity). The negradients resulting from back projection of the multiple photopeaks are combined. The image volume is updated by adding the conjugate gradient resulting from the combined negradients. For the update, the conjugate gradient is multiplied by an optimal step size based on the combined negradients.

This reconstruction scheme combines multiple photopeaks in one image volume for quantitative SPECT. Projecting for each photopeak with its system matrix or projection operators and combining the feedback from multiple photopeaks addresses the challenge of quantitative summation from multiple photopeaks where traditional method fails.

Figure 1:
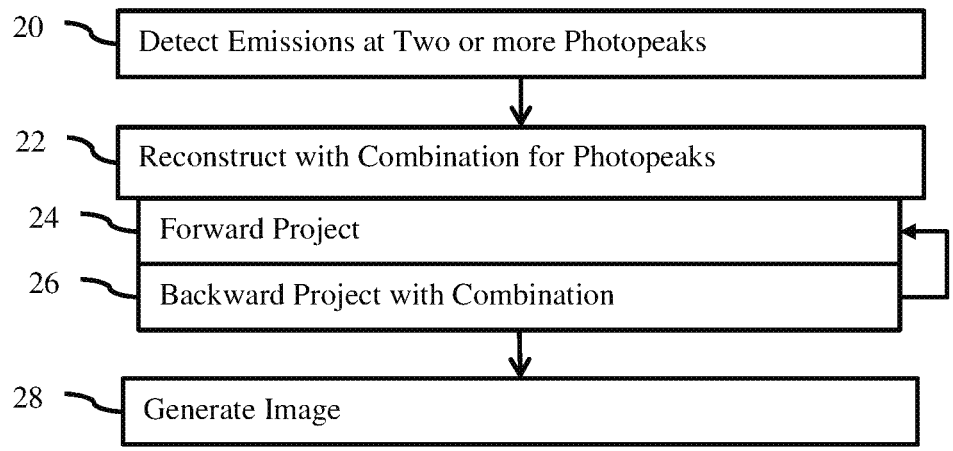
FIG. 1 is a flow chart diagram of one embodiment of a method for quantitative SPECT imaging with multiple photopeaks.

FIG. 1 shows one embodiment of a method for quantitative SPECT with multiple photopeaks. The photopeaks are peaks in the emission energy spectrum of the radioisotope. By combining information from the different photopeaks in reconstruction, a single image or volume is reconstructed.

The information is combined by forward and back projecting for the different photopeaks, but combing gradient information from the multiple photopeaks to update the image or object volume in each iteration.

The method is applied for a given scan of a given patient. The patient includes a radiotracer with an isotope emitting energies at different photopeaks. The emissions are detected at different energy ranges for the different photopeaks. The SPECT system performs quantitative SPECT based on the emissions at the different photopeaks.

Figure 2:
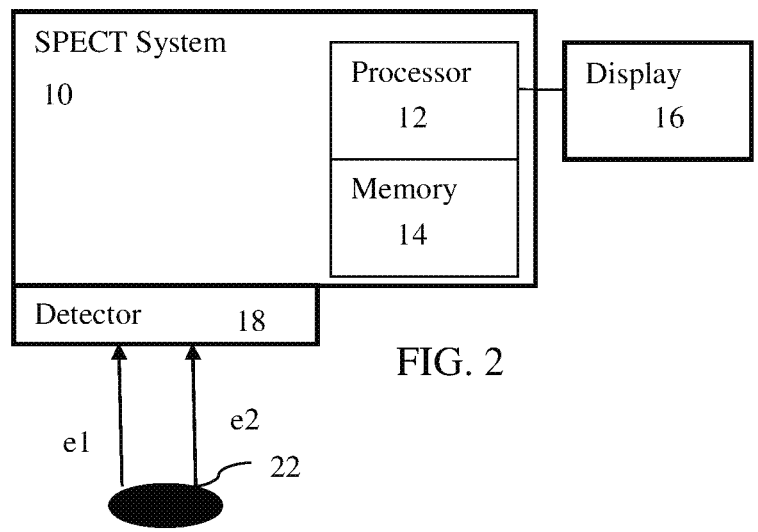
FIG. 2 is a block diagram of a system, according to one embodiment, for quantitative SPECT imaging with multiple photopeaks.

The acts are performed by the system of FIG. 2 or a different system. A detector, such as a gamma camera detects emissions in act 20. A processor, such as a SPECT system computer, reconstructs in act 22. The processor or a graphics-processing unit generates an image in act 28. Other devices may perform any of the acts.

Additional, different, or fewer acts may be performed. For example, act 20 is not provided where the detected emissions are stored or transferred from memory. As another example, act 28 is not provided where the reconstructed object is used for purposes other than imaging, such as to calculate a quantity. In other examples, acts related to positioning the patient, configuring the SPECT scanner, rotating the detector about the patient, and/or SPECT imaging are provided. The acts are performed in the order shown or a different order.

In act 20, emissions from a patient are detected. The activity concentration in a patient having received a radiotracer is determined as part of reconstruction by a quantitative SPECT system. After ingesting or injecting the radiotracer into the patient, the patient is positioned relative to a SPECT detector, and/or the SPECT detector is positioned relative to the patient. Emissions from the radiotracer within the patient are detected over time. A collimator in front of the detector limits the direction of photons detected by the SPECT detector, so each detected emission is associated with an energy and line or cone of possible locations from which the emission occurred. The lateral position of the line or cone relative to the detector may likewise be determined. The SPECT detector may be rotated or moved relative to the patient, allowing detection of emissions from different angles and/or locations in the patient.

The SPECT detector includes photomultiplier tubes or other photon detectors layered with a scintillation crystal. The photomultiplier tubes are arranged along a rectangular or other grid to provide a two-dimensional planar array for detecting gamma radiation. Other types of detectors may be used, such as any gamma detector.

The emissions are at different energies or photopeaks. Energies at two or more ranges are detected, where each energy range corresponds to the photopeaks of interest. The energies are for chosen ranges whether ranges from a continuous energy spectrum, from different major photopeaks, and/or from different minor photopeaks. For example, for I-123, there is a single main emission energy peak at 159 keV and many minor emission high-energy peaks. Rather than use a single photopeak acquisition energy window around 159 keV, two ranges of emission energy are detected—one for emission energy peak 159 keV and another for all high-energy emission peaks. In another example, a radionuclide with different emission energies is used. For example, I-123, Lu-177 or In-111 is used. Lu-177 emits with photopeaks at 113 kv and 208 kv. The emissions for energy ranges around those photopeaks are detected. Other photopeaks may not be included or may be included within the energy range set around one of the peaks being used.

By applying an energy threshold, emissions from different photopeaks or corresponding energy ranges are isolated. A different set of counts is provided for each of the different energy ranges. For example, two sets of counts of emissions are provided for two photopeaks or ranges about the photopeaks. Three or more different ranges of emission energies or about different photopeaks may be used. Each of the sets of emissions is a set of measured projection data for the respective photopeak.

In act 22, reconstruction is performed using the acquired projection data. The projection data represents the detected emissions. A processor of a SPECT system reconstructs the image or object that represents the emission distribution in the patient. The quantity or amount of uptake for each location (e.g., voxel) may be estimated as part of the reconstruction. The SPECT imaging system estimates the activity concentration of an injected radiopharmaceutical or tracer for the different locations. In quantitative SPECT, the goal is to estimate the activity concentration in kBq/ml of the tracer (i.e., isotope) that was injected into and distributed within the patient.

Any now known or later developed reconstruction methods may be used, such as based on Maximum Likelihood Expectation Maximization (ML-EM), Ordered Subset Expectation Maximization (OSEM), penalized weighted least squares (PWLS), Maximum A Posteriori (MAP), multi-modal reconstruction, non-negative least squares (NNLS), or another approach.

The reconstruction is iterative. The iterative reconstruction forward projects a current estimate of the volume or image (e.g., object space) to projection space using a system matrix or forward projectors representing the detection. Since the detected emissions are in a projection space (e.g., generally known location in two-dimensions but not three), the forward projection of the current volume is compared to the detected or measured emissions. This comparison is tested for accuracy with a merit function (e.g., ML-EM or NNLS). If sufficiently accurate and/or having no further increase in accuracy, the iteration ceases and the current volume is output as the reconstructed volume. If the merit function indicates insufficient or improving accuracy, a difference between the forward projection and the detected emissions is backward projected. This backward projection provides a gradient or change for the volume. The direction and step size is determined for the change and is applied to update the volume. The process is then repeated for another iteration of the reconstruction.

Where multiple photopeaks are used, the reconstruction is performed with forward and backward projection separately for each photopeak or emission energy range. Even with this separation, a single volume is reconstructed. The gradient or change from the backward projections for the different photopeaks is combined to provide one update of the volume or image space based on feedback from the multiple photopeaks.

In FIG. 1, the reconstruction of act 22 is represented by repetition of the forward projection in act 24 and the back projection of act 26. Additional acts may be provided.

In act 24, the processor forward projects the current image or volume to a projection space. The forward projection multiplies a system matrix or projection operators with the current volume to emulate the detection by the SPECT system.

The forward projection is performed separately at each of the multiple energy ranges or photopeaks. The forward projection may be represented as:

$$D_i = H_i I = \alpha_i P_i A_i I \quad (1)$$

where i is an index of the photopeak, $D_i$ is the detected emissions, $H_i$ is the system matrix or set of projection operators (e.g., $\alpha_i$, $P_i$, and $A_i$), $\alpha_i$ is sensitivity, $P_i$ is the point response function (PRF), $A_i$ is the attenuation, and I is the image (e.g., volume or set of voxels in object space). Additional, different, or fewer projection operators modeling operation of the SPECT system with a given patient for a given isotope may be used. Separately forward projecting the volume for different energy ranges or photopeaks results in different sets of forward projected data.

The reconstruction includes projection operators (i.e., forward projector) that incorporate the effects of the gamma camera on the photons (i.e., collimation and detection process) for a patient and isotope. In the reconstruction, the forward projector contains a model of the imaging formation process. The image formation model includes the interaction of photons with patients (e.g., attenuation and scatter), the collimation-detection process (e.g., collimator detector response including collimator geometric response, septal penetration and scatter, partial deposition in crystal and detector intrinsic resolution), and related radionuclide properties (e.g., emission abundances).

The system matrix is the mathematical representation of the projection from the object space to the projection space (e.g., forward projector). In some SPECT systems, such as SPECT for small animal imaging, the system matrix is actually stored and used directly in each iteration to calculate the projection data model from current estimate of the activity distribution. In most clinical SPECT systems, due to the very large dimension of the system matrix, the system matrix is not stored. Instead, a series of mathematical projection operators, collectively called the forward projector, are performed in each iteration, which mathematically provides multiplication by the system matrix.

One or more of the projection operators depend on the energy or energy range. As a result, the separate forward projection of the same volume results in different forward projections. Any of the projection operators or a system matrix formed therefrom may be dependent on the photopeaks. For use with emissions at two or more energies, since the various image-degrading effects (e.g., scatter, attenuation, and/or collimator-detector response function) are different for different energy ranges, the image formation process for photons at different energy ranges is modeled separately. One model that handles the scatter, attenuation, and/or collimator-response function differently for different energy provides separate models.

For radionuclides emitting multiple discrete energy peaks, one model may be applied for one emission peak or a combination of several peaks. For example, for Lu-177, in addition to two main photopeaks at 113 keV and 208 keV, there are two other minor photopeaks at 250 keV and 321 keV. Acquisition energy windows may not be provided around these two minor photopeaks, but the energies of one or more of the minor photopeaks may still contribute to the two acquisition energy windows around the two major photopeaks.

The results of the forward projection are checked with the merit function. Any reconstruction merit function may be used, such as the Mighell chi square merit function. The results are checked against the actual detected emissions in the projection or scan space.

Since multiple photopeaks are used, the forward projection for each photopeak or emission energy range is compared to the detected emissions for that photopeak. The sum, average, or other combination of the results of the comparisons is used to determine whether reconstruction is complete. In one embodiment, the merit function based on multiple photopeaks is represented as:

$$X^2 = \Sigma_i (H_i I - D_i)^T W_i (H_i I - D_i) \quad (2)$$

where $X^2$ is the chi square, T is the transpose, and $W_i$ is a weighting function. Any weighting function may be used, such as Mighell's chi square if W is the inverse of $D_i$. The difference in the forward projection $H_i I$ with the detected emission $D_i$ is weighted and multiplied with the transpose of the difference. This operation is performed for each photopeak i being used. The results from the different photopeaks are summed to provide the chi square value. Other functions, merit functions, or combinations from the different emission energies may be used.

In act 26, a feedback is backward projected. The feedback is computed by comparing detected emissions with the forward projection. This feedback is backward projected from the projection space to the image space of the volume. The feedback may be a correction or difference, ratio, or other relationship from the comparison.

The backward projection uses projection operators. A transpose of the system matrix or projection operators is applied to convert from the projection space to the image space. The transpose of the same projection operators used for the forward projection are applied. Where at least one of the projection operators is energy dependent, the corresponding transpose is also energy dependent. Since the transpose of the backward projection are energy dependent, different transposed projection operators are used for the different photopeaks or energy ranges.

The feedback to be back projected is also performed separately for the different energy ranges or photopeaks. For each of the multiple photopeaks, the processor backward projects a difference of the detected emissions for the respective photopeak with the forward projection for the respective photopeak. The different sets of detected emissions are differenced from the different forward projections, respectively. For example, the forward projection at an energy range including 113 keV is subtracted from the detected emissions at the energy range including 113 keV, and the forward projection at an energy range including 208 keV is subtracted from the detected emissions at the energy range including 208 keV. The backward projection is performed separately for each of the multiple emission energies with corresponding transposes of the operators for the respective energy.

The backward projection may be represented as:

$$G^{new} = \Sigma_i H_i^T W_i (D_i - H_i I) \quad (3)$$

where $G^{new}$ is the negradient. The negradient for each photopeak i is calculated as a weighted, $W_i$, transpose of the projection operators $H_i^T$ of a feedback, $D_i - H_i I$, of the forward projection, $H_i I$, from the detected emissions $D_i$. Other functions may be used, such as other gradients or back projected ratio of detected emissions over projection in MLEM.

The results from the backward projecting for each photopeak of interest are combined. The backward projection of the comparison provides feedback on how the current image or volume should be changed to better approximate the detected emissions. Since a single volume is used, the feedbacks form the different emission energy ranges are combined matrix for the volume. Any combination may be used, such as summation represented in equation (3). The negradients from the back projections for the different photopeaks are summed.

The combined negradient is used to correct the image or volume. The correction uses a conjugate gradient. In one embodiment, the conjugate gradient is calculated as:

$$K^{new} = \gamma K^{old} + G^{new} \quad (4)$$

where an old conjugate gradient, $K^{old}$, is combined (e.g., summed) with the combined negradients, $G^{new}$, to provide a new conjugate gradient, $K^{new}$. "Old" is used in the sense of from a previous or most recent iteration, and "new" is used for the current or next iteration of the reconstruction. The old conjugate gradient is weighted by $\gamma$. $\gamma$ may be any function, such as:

$$\gamma = \frac{(G^{new} - G^{old})^T G^{new}}{\|G^{old}\|^2} \quad (5)$$

The conjugate gradients are a function of the multiple photopeaks since the negradient is a function of the back projections at the different emissions energy ranges. Other gradients, other weights, and/or functions may be used.

The conjugate gradient, representing feedback combined from the multiple separately detected photopeaks, is used to correct the current volume or image. The volume is updated in an effort to better reflect the three-dimensional distribution of the radioisotope that results in the emissions detected in the projections space. In one embodiment, the update is represented as:

$$I^{new} = I^{old} + xK^{new} \quad (6)$$

where x is a step size. The conjugate gradient indicates a direction of change to the old image, and the step size indicates an amount of change. Other update functions may be used. Any step size function may be used, such as:

$$x = \frac{\sum_i (H_i K^{new})^T W(D_i - H_i I)}{\sum_i \|H_i K^{new}\|^2}. \quad (7)$$

As represented by the arrow returning from act 26 to act 24, the process repeats for one or more iterations of the reconstruction. The updated image or volume is forward projected in act 24 again for each of the photopeaks. The resulting forward projections are tested with the merit function. If reconstruction is not complete, then feedback for updating the volume is determined by back projecting in act 26. The differences from the multiple photopeaks are back projected and the resulting negradients for the different energy ranges are combined for correcting the single volume or image. The iterations continue until the forward projection of the volume provides a sufficient match with the detected emissions.

Once the reconstruction is complete, an image is generated. An image of the patient or part of the patient is generated from the reconstruction resulting from act 22. The results of the reconstruction represent a distribution of emissions or counts of emissions in three-dimensions. For qualitative SPECT, this distribution is used to generate an image. For quantitative SPECT, the activity concentration for each location (e.g., voxel) is determined. The reconstruction provides voxel values representing activity concentration. The activity concentration in a patient having received the liquid radiotracer is determined as part of reconstruction by the functional imaging system. In quantitative SPECT, the goal is to estimate the activity concentration in kBq/ml of the tracer (i.e., isotope) that was injected into and distributed within the patient. The projection operators include calibration information, and the detector sensitivity, such as the system specific sensitivity to the liquid radiotracer used in the patient.

After reconstruction, specific uptake values (SUVs) may be calculated by the processor. The activity concentration of the reconstruction represents the amount of uptake at each location. This amount of uptake is a measure of emitted radiation, so is not normalized for the radiation dose provided to the patient. As a result, comparing uptake from different times may not be useful unless the same does is provided. By calculating the SUV, uptake normalized for dose is provided, allowing comparison of different measures.

The SUV for each location or for some of the locations is calculated. The SUV is a function of the activity concentration for that location and the dose. The activity concentration is divided by the injected dose value. Other functions may be used. For example, the SUV may be a function of the body mass or other physical characteristic of the patient. The uptake magnitude represented in the activity concentration is normalized for both dose and body mass.

An image is generated from the reconstructed object (e.g., whole patient or part of the patient). In one embodiment, data for one or more (e.g., multi-planar reconstruction) planes is extracted (e.g., selected and/or interpolated) from a volume or voxels and used to generate a two-dimensional image or images. In another embodiment, a three-dimensional rendering is performed. Projection or surface rendering is used to create a representation of the volume or part of the patient from a given viewing direction on the two-dimensional screen.

The image is a quantitative SPECT image. Any quantitative SPECT imaging may be provided, such as providing an image where the user may determine a value for activity concentration for any selected location represented in the image. The image may include a number, text, graph, chart, or other representation of specific uptake and/or activity concentration quantities for one or more locations. Alternatively, the image is a qualitative SPECT image that indicates relative activity concentration distribution in the patient.

Any SPECT image may be displayed alone, adjacent to a computed tomography (CT) image, or overlaid on a CT image (e.g., color for SPECT and grayscale for computed tomography). Multi-modality images with magnetic resonance, ultrasound, x-ray, or other modalities may be used.

FIG. 2 shows a system for SPECT imaging with multiple emission energies. The system is a quantitative or qualitative SPECT system. The system implements the method of FIG. 1 or other method.

The system includes an SPECT system 10, a processor 12, a memory 14, and a display 16. The processor 12, memory 14, and/or display 16 are part of the SPECT system 10 or are separate (e.g., a computer or workstation). Additional, different, or fewer components may be provided. For example, the system is a computer without the SPECT system 10. As another example, user input, patient bed, or other SPECT related devices are provided. Other parts of the system may include power supplies, communications systems, and user interface systems.

The SPECT system 10 includes a detector 18. Other components may be provided, such as collimator. Any now known or later developed SPECT system 10 may be used.

The detector 18 is a gamma camera connected with a gantry. The gamma camera is a planar photon detector, such as having crystals or scintillators with photomultiplier tubes or other optical detector. The gantry rotates the gamma camera about the patient. During scanning of a patient, emission events are detected with the camera at different positions or angles relative to the patient.

The SPECT system 10, using the detector 18, detects emissions from the patient 22 for measuring uptake or physiological function. The detector 18 detects emissions at different energies ranges, e1 and e2, from the patient 22. The energy ranges correspond to different photopeaks, such as major and/or minor photopeaks. In other embodiments, the different or multiple energy ranges overlap, do not overlap, and/or are for parts of the energy spectrum without a particular photopeak. For imaging uptake in a patient, the detector 18 detects emissions from the patient. The emissions occur from any location in a finite source (i.e., the patient). The radiotracer in the patient migrates to, connects with, or otherwise concentrates at specific types of tissue or locations associated with specific biochemical reactions. As a result, a greater number of emissions occur from locations of that type of tissue or reaction.

The detector 18 applies energy thresholds or other process to detect emission energy at the multiple energy ranges. The emissions for the different emission energy ranges are separately counted.

The processor 12 is a general processor, digital signal processor, graphics processing unit, application specific integrated circuit, field programmable gate array, digital circuit, analog circuit, combinations thereof, or other now known or later developed device for processing emission information. The processor 12 is a single device, a plurality of devices, or a network. For more than one device, parallel or sequential division of processing may be used. Different devices making up the processor 12 may perform different functions, such as one processor (e.g., application specific integrated circuit or field programmable gate array) for reconstructing and another (e.g., graphics processing unit) for generating an image. In one embodiment, the processor 12 is a control processor or other processor of SPECT system 10. In other embodiments, the processor 12 is part of a separate workstation or computer.

The processor 12 operates pursuant to stored instructions to perform various acts described herein, such as reconstructing of act 22 and generating an image of act 28. The processor 12 is configured by software, firmware, and/or hardware to reconstruct a volume or object from emissions in different emission energy ranges. Feedback or information from the multiple photopeaks is combined or used to correct a single volume representation of the object. The combination is performed as part of the reconstruction, such as within the iteration loop.

The SPECT system 10, using the processor 12 or another processor, is configured to reconstruct the imaged volume from the detected data. Any reconstruction may be used to estimate the activity concentration or distribution of the tracer in the patient. The SPECT system 10 accesses the detected emission events from the memory 14, from the detector 18, or buffers to reconstruct.

The detected emissions are used to reconstruct the distribution of the radioisotope in three dimensions. Forward and backward projection are used iteratively until a merit function indicates completion of the reconstruction. Since the emissions are counted separately for the different emission energy ranges or photopeaks, the forward and backward projection operations are performed separately for each energy range or photopeak. As part of backward projection or part of updating the volume or current estimate of the distribution using results from backward projection, feedback from the different energy ranges is used. For example, based on the back projection, a conjugate gradient is computed and used to update the current estimate of the distribution. The conjugate gradient is a function of a sum of back projections of feedback between the forward projected distribution and the detected emissions from different energy ranges or photopeaks. By forward projecting and backward projecting separately for each energy range or photo peak, different negradients are provided for updating the image. These different negradients are combined to provide the update for the current distribution. The conjugate gradient used to update the direction and step size of the distribution is a function of the emissions at the various emission energy ranges or photopeaks.

The processor 12 generates one or more images based on the reconstruction. Any given image represents the emissions from the two or more energies. The image shows the spatial distribution, such as with a multi-planar reconstruction or a volume rendering. For quantitative SPECT, the image represents accurate measures (e.g., in Bq/ml) of the activity concentration based on emissions from the same isotope at different energies. Alternatively or additionally, the image shows a quantity or quantities (e.g., alphanumeric) representing the activity concentration or specific uptake values for one or more locations or regions.

The display 16 is a CRT, LCD, plasma screen, projector, printer, or other output device for showing an image. The display 16 displays an image of the reconstructed functional volume, such as showing activity concentration as a function of location. The uptake function of the tissues of the patient is represented in the image. Alternatively or additionally, any quantities derived by the processor 12 may be displayed, such as uptake values and/or change in uptake value. Other quantities may be determined, such as average uptake value or activity concentration for a region, maximum uptake value, peak uptake value in a predetermined unit volume, variance in activity concentration, or total uptake.

The detected emission events, counts, energy level, location, or other SPECT detection information are stored in the memory 14. The memory 14 may store data at different stages of processing, such as counts, raw data representing detected events without further processing, filtered or thresholded data prior to reconstruction, forward projections, backward projections, differences, projection operators, transposed operators, a measure of completeness of reconstruction, reconstructed data, filtered reconstruction data, system matrix, thresholds, results of calculations, an image to be displayed, an already displayed image, or other data. The data is stored in any format. The memory 14 is a buffer, cache, RAM, removable media, hard drive, magnetic, optical, database, or other now known or later developed memory. The memory 14 is a single device or group of two or more devices. The memory 14 is part of SPECT system 10 or a remote workstation or database, such as a PACS memory.

The memory 14 is additionally or alternatively a non-transitory computer readable storage medium with processing instructions. The memory 14 stores data representing instructions executable by the programmed processor 12. The instructions for implementing the processes, methods, and/or techniques discussed herein are provided on non-transitory computer-readable storage media or memories, such as a cache, buffer, RAM, removable media, hard drive, or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for quantitative single photon emission computed tomography (SPECT) with multiple photopeaks, the method comprising:
    detecting, with a SPECT detector, emissions from a patient, the emissions being at different photopeak ranges of an isotope with respective multiple photopeaks;
    forward projecting, in reconstruction from the emissions, for a first of the different photopeak ranges;
    forward projecting, in the reconstruction from the emissions, for a second of the different photopeak ranges;
    backward projecting in the reconstruction from the emissions, the backward projecting combining feedback from the first and second photopeak ranges, and wherein backward projecting comprises combining conjugate gradients from the multiple photopeaks; and
    generating an image as a function of the reconstruction.

2. The method of claim 1 wherein detecting comprises detecting the emissions from a radionuclide with the different photopeaks, the radionuclide being in the patient.

3. The method of claim 1 wherein detecting the emissions comprises detecting a first set of emissions at the first photopeak range and a second set of emissions at the second photopeak range, and wherein backward projecting combining the feedback comprises summing first and second feedbacks relative to the first and second sets, respectively.

4. The method of claim 1 wherein forward projecting for the first and second photopeak ranges comprises forward projecting with projection operators, which are dependent on the photopeaks, and wherein backward projecting comprises backward projecting with the projection operators, which are dependent on the photopeaks.

5. The method of claim 1 wherein forward and backward projecting comprise reconstructing with a single image volume for the different photopeak ranges.

6. The method of claim 1 wherein backward projecting comprises computing a negradient as a sum of backward projections at the multiple photopeaks.

7. The method of claim 1 wherein backward projecting comprises:
    for each of the multiple photopeaks, backward projecting a difference of the detected emissions with a forward projection for the respective one of the multiple photopeaks; and
    combining results of the backward projecting.

8. The method of claim 7 wherein the projection operators of the backward projecting, the forward projections, and the detected emissions are a function of the photopeak.

9. The method of claim 1 wherein generating the image comprises generating (28) a quantitative SPECT image.

10. The method of claim 1 wherein generating the image comprises generating the image as representative of a patient from which the emissions are detected.

11. The method of claim 1 wherein generating the image comprises generating an image of a quantity representing activity concentration.

12. In a non-transitory computer readable storage medium having stored therein data representing instructions executable by a programmed processor for single photon emission computed tomography with multiple emission energies, the storage medium comprising instructions for:
    projecting separately for each of the multiple emission energies with operators for that energy; and
    combining gradients from results of the projecting for the multiple emission energies.

13. The non-transitory computer readable storage medium of claim 12 wherein projecting comprises backward projecting from a projections space to an image space.

14. The non-transitory computer readable storage medium of claim 12 wherein projecting separately comprises, for each of the emission energies, determining a difference of a forward projection with the operators for that energy from measured emissions for that energy, and multiplying the difference by a transpose of the operators for that energy.

15. The non-transitory computer readable storage medium of claim 14 wherein combining comprises summing the results of the multiplying for the multiple emission energies.

16. The non-transitory computer readable storage medium of claim 12 wherein combining comprises combining negradients as the results from the projecting.

17. The non-transitory computer readable storage medium of claim 12 further comprising:
    forward projecting separately at each of the multiple energies; and
    repeating the projecting and combining with an output of the forward projections at the multiple energies.

18. A single photon emission computed tomography (SPECT) system, the SPECT system comprising:
    a detector for detecting emissions at first and second photopeaks from an isotope emitting at the first and second photopeaks;
    a processor configured to reconstruct a distribution of the emissions in three dimensions from the emissions, the reconstruction using a conjugate gradient, the conjugate gradient being a function of the emissions at both the first and second photopeaks; and
    a display configured to display an image from the reconstruction.

19. The SPECT system of claim 18 wherein the processor is configured to backward project separately for the emissions at the first and second photopeaks and sum results from the separate backward projections, the conjugate gradient being a function of the sum.

20. A method for quantitative single photon emission computed tomography (SPECT) with multiple photopeaks, the method comprising:

detecting, with a SPECT detector, emissions from a patient, the emissions being at different photopeak ranges of an isotope with respective multiple photopeaks;

forward projecting, in reconstruction from the emissions, for a first of the different photopeak ranges;

forward projecting, in the reconstruction from the emissions, for a second of the different photopeak ranges;

backward projecting in the reconstruction from the emissions, the backward projecting combining feedback from the first and second photopeak ranges, and wherein backward projecting comprises:

for each of the multiple photopeaks, backward projecting a difference of the detected emissions with a forward projection for the respective one of the multiple photopeaks, and combining results of the backward projecting; and generating an image as a function of the reconstruction.

21. The method of claim 20 wherein the projection operators of the backward projecting, the forward projections, and the detected emissions are a function of the photopeak.

* * * * *